United States Patent [19]

Roberts et al.

[11] Patent Number: 5,004,682

[45] Date of Patent: Apr. 2, 1991

[54] METHOD AND KIT FOR DETECTING LIVE MICROORGANISMS IN CHLORINE- OR BROMINE-TREATED WATER

[75] Inventors: Katherine P. Roberts, Derby; Jon R. Geiger, West Hartford; Jayne F. Carney, Wallingford, all of Conn.

[73] Assignee: Olin Corporation, Cheshire, Conn.

[21] Appl. No.: 115,313

[22] Filed: Nov. 2, 1987

[51] Int. Cl.$^5$ .......................... C12Q 1/68; C12Q 1/02; G01N 1/18; C12N 1/06

[52] U.S. Cl. .......................................... 435/6; 435/29; 435/30; 435/259; 435/261; 436/501; 436/17; 436/174; 436/177; 436/178; 436/164; 436/172

[58] Field of Search ........................ 435/6, 29, 34, 805, 435/810; 935/77, 78; 436/94, 164, 172, 177, 501, 178, 174; 536/27, 26, 28

[56] References Cited

U.S. PATENT DOCUMENTS

| | | | |
|---|---|---|---|
| 4,233,404 | 11/1980 | Baier | 435/803 |
| 4,358,535 | 11/1982 | Falkow et al. | |
| 4,431,545 | 2/1984 | Pall et al. | |
| 4,623,723 | 11/1986 | Keller et al. | 536/27 |
| 4,689,295 | 8/1987 | Taber et al. | 435/34 |
| 4,785,086 | 11/1988 | Rashtchian et al. | |
| 4,792,519 | 12/1988 | Blackburn et al. | 435/6 |
| 4,816,389 | 3/1989 | Sansonetti et al. | 435/6 |

FOREIGN PATENT DOCUMENTS 0170584  2/1986  European Pat. Off.

OTHER PUBLICATIONS

Margolin, Aaron B., "The Development of a Dot Blot Assay Using Gene Probes for the Detection of Enteroviruses in Water", UMI Dissertation Information Service, 1987, pp. 76 and 104–110.

Margolin et al, "Use of cDNA Dot-Blot Hybridization Techniques for Detection of Enterviruses in Water", Proc.—AWWA Water Qual. Technol. Conf., 1985, pp. 13, 87–95; Chem. Abst. 105; 93823y.

Grimont et al, "DNA Probe Specific for *Legionella pneumophila*", 1985, p. 431.

Worley et al, "A New Water Disinfectant; a Comparative Study", Ind. Eng. Chem. Prod. Res. Dev., 1983, pp. 716–718; Chem. Abst. 99:181208m.

Shapiro et al, "Method for the Isolation of High Molecular Weight Nuclear DNA From Lymphocytes Using Ultrafiltration Membrane", 1982, pp. 1339–1342; Chem. Abst. 98;2464n.

Kowal et al, "Disinfection of Water and Biologically Treated Sewage by Chlorine, Ozone, and Chlorine Dioxide", Gaz. Woda. Tech. Sanit., 1980, pp. 319–320; Chem. Abst. 95;67300c.

White, C. G., "Chlorination of Potable Water", Handbook of Chlorination, 1972, pp. 278–280.

Echeverria, P., Seriwatana, J. Chityothin, O., Chiacumpa, W., and C. Tirapat; Journal of Clinical Microbiology, vol. 16, No. 6, pp. 1086–1090 (1982).

American Water Works Association's "Technology Conference Proceedings; Advances in Water Analysis and Treatment", Gerba et al, Portland, Ore., p. 1025–1041 (1986) entitled Low Cost Rapid Methods for Enterovirus Detection in Water.

*Primary Examiner*—Robert A. Wax
*Assistant Examiner*—Stephanie W. Zitomer
*Attorney, Agent, or Firm*—Dale Lynn Carlson

[57] ABSTRACT

A water monitoring system, and more particularly a method and kit for detecting the presence of live undesirable or indicator microorganisms in water after treatment of the water with chlorine or bromine.

14 Claims, No Drawings

METHOD AND KIT FOR DETECTING LIVE MICROORGANISMS IN CHLORINE- OR BROMINE-TREATED WATER

FIELD OF THE INVENTION

This invention relates generally to water monitoring systems, and more particularly to a method and kit for detecting the presence of only living undesirable or indicator microorganisms in water after treatment of the water with chlorine or bromine.

BACKGROUND OF THE INVENTION

Chlorine is used extensively in the United States and foreign countries to treat drinking water supplies. The chlorine acts as a biocide to destroy undesirable microorganisms. The efficacy of the chlorine treatment is monitored by periodic checking of the treated water for the presence of selected, living, indicator organisms (e.g., coliforms). These serve to indicate the possibility of potable water supply contamination. Conventional microorganism detection methods used to monitor the treated water require the growth of the microorganisms in culture media to a detectable level, followed by confirmatory tests for the existence of specific microorganisms. These conventional detection methods may take up to several days to complete.

A more rapid method for detecting the presence of live microorganisms in chlorine-treated water would be extremely useful to the water treatment industry. One possible detection technique, namely the use of monoclonal antibodies (referred to as "MAB"), has now been found by the present inventors to be unsuitable for such detection since the MAB technique does not distinguish between living and dead microorganisms in the chlorine-treated water. Since only living cells are potentially harmful, any test which does not distinguish living from dead cells will tend to give a so-called "false-positive" result when only the innocuous dead cells are present On this basis, the MAB technique is unacceptable for use (as described) in the water treatment industry In light of the foregoing, the discovery of a rapid microorganism detection method for use in chlorine-treated water which selectively detects living microbial cells would be highly desired by the water treatment industry

SUMMARY OF THE INVENTION

In one aspect, the present invention relates to a method for detecting the presence of live microorganisms in chlorine- or bromine-treated water comprising:
(a) lysing live microorganisms present in a sample of chlorine- or bromine-treated water and rendering constituent nucleic acid molecules single-stranded to provide single-stranded target nucleic acid molecules;
(b) contacting said single-stranded target nucleic acid molecules with single-stranded labelled probe nucleic acid molecules to cause hybridization thereof with a portion of said labelled probe nucleic acid molecules to form labelled hybridized probe/target nucleic acid molecules, and
(c) separating said labelled hybridized probe/target nucleic acid molecules from said single-stranded labelled probe nucleic acid molecules using separation means.

Typical separation means include ultrafiltration, membrane immobilization, or the use of hydroxylapatite.

In another aspect, the present invention relates to a kit for detecting the presence of live microorganisms in chlorine- or bromine-treated water comprising:
(a) a sample of single-stranded labelled probe nucleic acid molecules,
(b) a sample of live microorganisms in, or obtained from, chlorine-treated or bromine-treated water,
(c) a lysing medium for providing single-stranded target nucleic acid molecules from within said live microorganisms, and
(d) a medium (e.g., a membrane filter, ultrafiltration apparatus, or hydroxylapatite) for effecting separation of hybridized probe/target nucleic acid molecules from single-stranded labelled probe nucleic acid molecules.

DETAILED DESCRIPTION OF THE INVENTION

In accordance with the present invention, it has now been surprisingly discovered that nucleic acid probes can be used to detect the presence of only living microorganisms (as selectively distinguished from dead microorganisms) in chlorine- or bromine-treated water. This discovery is particularly surprising in view of the findings by the present inventors that monoclonal antibodies are unsuitable since they do not differentiate living versus dead microorganisms present in chlorine- or bromine-treated water. In addition, nucleic acid probes themselves are not suitable for use with hydrogen peroxide or formalin-treated water because nucleic acid probes do not distinguish live from hydrogen peroxide or formalin-killed cells.

The DNA or RNA from undesirable or indicator microorganisms, a portion of whose specific base sequence is generally known, is referred to herein as a target. The polynucleotide containing the label and expected to have a base sequence complementary to the target is referred to herein as a probe. DNA and RNA probes are single-stranded nucleic acid molecules generally synthesized by so-called gene machines or made using recombinant DNA methods. Probes are constructed so that the base sequences of the probe match (and lend themselves to hybridization with) complementary sequences on a target molecule. The joining together of both target and complementary probe polynucleotide by the mechanism of base pairing through hydrogen bonds between purine and pyrimidine bases is thus referred to herein as hybridization and the resultant complex is termed a hybridized nucleic acid molecule or hybridized probe/target molecule.

The nucleic acid probe will typically consist of chemically synthesized or biologically prepared DNA or RNA polynucleotides in the form of single-stranded sequences and single-stranded DNA or RNA. If synthesized, the single-stranded DNA or RNA probe is fabricated so that its nucleic acid base sequence is complementary to a region of the bacterial, viral, or protozoan target sequence.

As an alternative to synthesis, probe DNA or RNA can be isolated from biological sources and subsequently reacted with a labelling reagent of interest. Single-stranded DNA can be obtained directly from single-stranded viral genomes such as M13 or indirectly from double-stranded genomes or plasmids by strand separation. The size of such a probe will be controlled by enzymatic processing including exonuclease treatment of single-stranded DNA and restriction or Bal 31 nuclease digestion of double-stranded DNA.

In another alternative, the DNA probe can also be prepared enzymatically from appropriate nucleic acid substrates. For example, DNA could be obtained from mRNA using reverse transcriptase. RNA probes can be directly obtained from biological sources in the form of viral genomes (R17, F2, QB) or mRNA. Alternatively, the RNA can be enzymatically synthesized in vitro from appropriate templates. For example, phage RNA polymerase catalyzed transcription from a double-stranded DNA template such as a sequence cloned next to a phage promoter in an appropriate cloning vector would generate probe RNA.

The probe may be obtained from messenger RNA, from ribosomal RNA, or from cDNA obtained by reverse transcription of messenger RNA or ribosomal RNA with reverse transcriptase. Probe may also be obtained by cleavage of the genome, conveniently by endonuclease digestion, followed by cloning of the gene or gene fragment in accordance with known techniques. See, for example, Kornberg, DNA Replication, W. H. Freemen and Co., San Francisco, 1980, pp 670–679; So et al, Infect. Immun. 21:405–411, 1978. After isolation and characterization of the desired gene or DNA fragment, the gene or DNA fragment may be used for preparation of the probe or transcribed for production of RNA, which may then be used for preparation of the probe.

The probe will normally have at least 20 bases, more usually at least several hundred bases, and may have up to about 10,000 bases or more, usually having not more than about 5,000 bases. The probe sequence will be at least substantially complementary to a sequence characteristic of the microorganism of interest. The probe need not have perfect complementarity to the sequence to which it hybridizes; there may be 30 percent or more of mismatched pairs.

Prior to use in hybridization, each probe molecule is generally labelled with, for example, a radioactive tag, in order to permit detection of when and where hybridization has occurred. Either radioactive or nonradioactive probes may be used in the method and kit of the present invention. As an example, one radioactive probe method first involves incubating a membrane (that has single-stranded target sequences attached) with a radioactively labelled probe (usually phosphorus-32 ($^{32}P$)) consisting of a single strand of DNA or RNA with base sequences that are possibly complementary to the target sequences being studied. The probe hybridizes with only those target nucleic acids containing a complementary nucleic acid sequence. After hybridization, the membrane is washed and hybrids are detected by conventional autoradiography. The presence of characteristic hybrid nucleic acid on an autoradiogram is indicative of the presence of a specific target sequence.

Frequently, a polynucleotide probe will be utilized that has been labelled with an atom or inorganic radical, most commonly using radionuclides, but also perhaps heavy metals However, in some situations it may be feasible to employ an antibody which will bind specifically to the probe hybridized to the single-stranded target DNA. In this instance, the antibody would be labelled to allow for detection. The same types of labels which are used for the probe may also be bound to the antibody in accordance with known techniques.

Typical radioactive labels include $^{32}P$, $^3H$, $^{125}I$, $^{35}S$, $^{14}C$, or the like. However, any radioactive label may be employed which provides for an adequate signal and has sufficient half life. Other labels include ligands, which can serve as a specific binding member to a labelled antibody or to a specific binding protein, fluorescers, chemiluminescers, enzymes, antibodies, which can serve as a specific binding site for a labelled ligand, and the like. The probe may also contain a non-radioactive label molecule which can be a chromogenic, fluorogenic, luminescent dye molecule, magnetic particle, or an enzyme system capable of generating a chromogenic, fluorogenic, and/or luminescent product via appropriate substrates.

A biotinylated DNA probe using a biotinylated deoxyuridine triphosphate signal procedure can also be used for probe/target hybridization detection following hybridizations. This probe has also been used to signal probe nucleic acid hybridized to target nucleic acid immobilized on membranes. The detection of the hybridized biotinylated probe is accomplished by either fluorescent or enzyme amplification techniques.

The choice of the label can be governed by the effect of the label on the rate of hybridization and binding of the probe to the target DNA. It will be necessary that the label provide sufficient sensitivity to detect the amount of DNA available for hybridization. Other considerations will be ease of synthesis of the probe, ready availability of instrumentation, ability to automate, convenience, and the like.

The manner in which the label is bound to the probe will depend upon the nature of the label. For a radioactive label, a wide variety of techniques can be employed. Commonly employed is nick translation with an -$^{32}P$-dNTP or terminal phosphate hydrolysis with alkaline phosphatase followed by labelling with radioactive $^{32}P$ employing -$^{32}P$-NTP and T4 polynucleotide kinase. Alternatively, nucleotides can be synthesized where one or more of the elements present are replaced with a radioactive isotope, e.g., hydrogen with tritium. If desired, extensions of the probe strand with a simple repetition of one nucleotide (and therefore unlikely to be complementary to any target sequence) can be used to enhance the concentration of hybridized label.

Where other radioactive compounds are involved, various linking groups can be employed. A terminal hydroxyl can be esterified with inorganic acids, e.g., $^{32}P$ phosphate, or $^{14}C$ organic acids, or else esterified to provide linking groups to the label. Alternatively, intermediate bases may be substituted with activatable linking groups which can then be linked to a label.

Ligands and antiligands may be varied widely. Where a ligand has a natural receptor, namely ligands such as biotin, thyroxine, and cortisol, these ligands can be used in conjunction with labelled naturally occurring receptors. Alternatively, any compound can be used, either haptenic or antigenic, in combination with an antibody.

Enzymes useful as labels include hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The amount of labelled probe which is present in the hybridization solution will vary widely, depending upon the nature of the label, and the stringency of the hybridization. Generally, substantial excesses over a stoichiometric amount of the probe will be employed to enhance the rate of hybridization and to allow the quantifying of the amount of target sequences present.

Using the method and kit of the present invention, live microorganisms (particularly bacteria, protozoa, mold, and yeast) present in chlorine- or bromine-treated water are lysed with a lysing solution to expose the microorganism's DNA or RNA and provide therefrom a single-stranded nucleic acid moiety. For bacteria, lysing is typically carried out using a lysozyme, typically chicken egg white lysozyme, followed by a series of quick freezing and thawing steps or by treatment with a surfactant to disrupt the cell membrane. For viruses and protozoa, the nucleic acid therefrom is suitably exposed using a protease, such as proteinase K or by phenol extraction. After lysing, the released nucleic acid is rendered single-stranded by heating, and the single-stranded nucleic acid from the various microorganisms (some of which may be target nucleic acid from undesirable or indicator micro-organisms) is contacted with single-stranded probe nucleic acid for possible hybridization thereof.

As indicated above, suitable probes have base sequences complementary to complementary sequences on undesirable (e.g., potentially harmful) or indicator microorganisms that may be present in chlorine- or bromine-treated water.

In the hybridization, the single-stranded target nucleic acid derived from microorganisms in a chlorine- or bromine-treated water sample is reacted with the probe under conditions where hybridization of the probe with the target microorganism DNA can occur.

The particular hybridization technique employed is not a critical element of the present invention. Various hybridization solutions may be employed, comprising from about 20 to 60, preferably 40 to 50, volume percent of an inert polar organic solvent. A common hybridization solution employs about 50 percent formamide, about 0.05 to 0.5M sodium phosphate, and minor amounts of EDTA. Other additives may also be included, such as dextran sulfate of from about 100 to 1,000 dal and in an amount of from about 8 to 15 weight percent of the hybridization solution. Alternatively, aqueous solutions containing these salts and polymers and free of organic solvents such as formamide may be employed. The hybridization time employed can be one-half hour or less up to several hours or more as desired.

The extent of hybridization is affected by various factors, including temperature, probe concentration, probe length, ionic strength, time, and the like. As an illustrative example, the extent of hybridization can be varied by changing the polarity of the reactant solution by manipulating the concentration of formamide in the range of 0 to 50 percent. Alternatively, temperatures can be varied in the range of about 20° to 85° C., usually 30° to 75° C.

After hybridization and before the hybridized probe/target nucleic acid molecules can be identified based upon the presence of the label on the probe, the unhybridized single-stranded labelled probe molecules must be separated out. Otherwise, this latter material will act as "background noise," interfering with attempts to identify the hybridized material. Conventionally utilized commercial methods for effecting this separation of hybridized probe molecules from unhybridized single-stranded probe molecules can be used in the method of the present invention. These techniques can usually involve immobilizing the target nucleic acid on a membrane which is reactive with nucleic acids. Such membranes bind all nucleic acids nonselectively. In view of this nonselectivity characteristic, the active sites on the membrane are blocked before probe nucleic acid is added. Thus, the membrane is treated with various blocking agents (as is known) after the target DNA is affixed to the membrane in order to prevent nonspecific adhesion of the probe nucleic acid. In this manner, washing the membrane after hybridization will remove unhybridized probe only, and leave the hybridized probe/target affixed to the membrane.

Alternatively, selective adsorption of double-stranded nucleic acids using hydroxylapatite is employed to separate the hybridized probe/target nucleic acid molecules from the unhybridized single-stranded labelled probe. The hydroxylapatite serves to effectively separate double- from single-stranded DNA based upon its selective affinity for double-stranded DNA under certain ionic strength conditions with ionic strength buffers, as described in more detail in Kohne, D. E., 1984, Patent Cooperation Treaty Patent Application WO 84/02721.

Other separation methods to recover and detect the hybridized probe/target molecules can be used with the present invention. For example, U.S. Pat. No. 4,599,303, the disclosure of which is incorporated herein by reference, discloses a method of first hybridizing and then forming covalent bonds between probe and target, disclosing at column 2, lines 55-61 thereof, several procedures for separating covalently crosslinked double-stranded probe-target complex from single-stranded probe. These procedures are described as including gel filtration, hydroxylapatite chromatography, enzymatic digestion, alkaline hydrolysis, and photoreversal or chemical reversal of uncrosslinked crosslinking molecules.

A preferred method for recovering and detecting hybridized probe/target nucleic acid molecules is disclosed in co-pending U.S. application Ser. No. 944,919, filed Dec. 22, 1986, and assigned to the same assignee as that of the present application. By this technique, the hybridized labelled probe/target is separated from unhybridized labelled probe by ultrafiltration. As used herein, the terms "ultrafiltration" and "ultrafiltering" denote filtration using a membrane filter having a sufficiently small pore size such that macromolecules of a particular molecular weight, typically from 50,000 to 1,000,000 daltons, are retained by the filter, thereby separating single-stranded nucleic acid from hybridized probe/target nucleic acid. This ultrafiltration is preferably conducted while centrifuging the mixture containing hybridized probe/target, thereby expediting the ultrafiltration process. Ultrafiltration is suitably effected using a membrane filter constructed of any solid network material such as, for example, cellulosic, acrylic, or other material that will not bind either nucleic acid or protein nonspecifically. Centrifugation, if used as a driving force for the ultrafiltration, is generally applied at 1000 to 3000 rpms at between 500 and 2000 RCF (relative centrifugal force), e.g. in a fixed-angle centrifuge rotor. Alternatively, more conventional ultrafiltration using pressure-driven membrane separation can be employed with pressures between 5 and 20 atmospheres.

Detection of the hybridized probe will normally be accomplished by measuring the amount of the label on the double-stranded molecule after hybridization. Various methods or protocols may be employed in measuring the amount of the labels on the hybridized probe/target molecules. These protocols include, for example, autoradiography, detection of radioactive decay in a scintillation counter or using a geiger counter, chemiluminescent assays, bioluminescent assays, and assays of enzymes linked either directly or indirectly to the probe, among others.

The method of the present invention employs a simple protocol, employs reagents which can be standardized and provided in commercial kits, and allows for rapid screening of a large number of samples.

In carrying out the method of the present invention, a sample of chlorine- or bromine-treated water suspected of containing the microbe(s) is provided from, for example, a drinking water testing station. The sample may have been pre-concentrated with microbes by using parallel flow or perpendicular flow filters. After lysing the microbe(s) and treating the released nucleic acid to render it single-stranded, such as by heating, the single-stranded DNA or RNA material is then hybridized with a labelled probe polynucleotide having a complementary base sequence. This hybridization generally takes place in the presence of an excess of probe relative to the amount of the known-sequence target to be hybridized. For example, a 100 fold to 1,000 fold excess of probe to specific target sequences will allow rapid hybridization of all target sequences. Such an excess also allows quantitative analysis of numbers of contaminating organisms in a single test.

As stated above, the kit of the present invention contains a sample of labelled probe, a sample of live indicator or undesirable microorganisms in (or obtained or derived from) chlorine- or bromine-treated water, a lysing medium, and a medium for effecting separation of hybridized probe/target nucleic acid molecules from unhybridized, single-stranded labelled probe nucleic acid molecules. Typically, the sample of indicator or undesirable (target) microorganisms will be provided by the kit user. The kit also preferably contains a wash solution (e.g., a phosphate-buffered 50 percent formamide solution) for washing away unhybridized labelled probe nucleic acid. If the probe is enzyme labelled, the kit also preferably contains an enzyme substrate and buffer solution to optimize the enzyme's catalytic activity and to allow signal development and/or enhancement of the label for identification of the hybridized probe/target nucleic acid molecules.

The method and kit of the present invention are especially useful for detecting the presence of live indicator or undesirable microorganisms in chlorine-treated or bromine-treated drinking water and other chlorine-treated or bromine-treated water for human or animal consumption, such as water for use in foods.

The following examples are intended to illustrate, but in no way limit the scope of, the present invention.

EXAMPLE 1

Hybridization of Radioactive Labelled DNA With Target Nucleic Acids From Chlorine-Killed *Escherichia coli*

The assay for this experiment was done with Gen Probe Inc.'s "Mycoplasma T.C. II Rapid Detection System Kit" and the bacterium *E. coli*. The kit contains: bacterial lysing agent in buffer, $^3$H-Mycoplasma DNA probe ($<1$ $\mu$Ci/4 ml), hydroxylapatite separation suspension, and a wash buffer. The Mycoplasma probe is a radioactive ($^3$H-labelled) cDNA probe against bacterial ribosomal RNA (rRNA). It has been tested against a wide variety of bacteria and was

*E. coli* cells ($10^7$/ml) were exposed to 32 phosphate buffer at a pH of 6.8 for either 5 minutes or 30 minutes at room temperature. The chlorine was inactivated with sodium thiosulfate and the cells lysed using lysozyme and heat to a temperature of 100° C. The remainder of the assay was performed following Gen-Probe's protocol. Briefly, this protocol was as follows:

The probe solution was added to the samples in scintillation vials and incubated at 72° C. After one hour, 5 ml of separation suspension containing hydroxylapatite was mixed with the sample. After five minutes at 72° C., samples were centrifuged for one minute. The supernatant was discarded and 5 ml of wash solution added. After five minutes at 72° C., samples were centrifuged, the supernatant was discarded and the retained probe (radioactivity) was measured.

Scintillation counting to measure the extent of hybridization was done with CytoScint (West Chem) in a Beckman LS-100C scintillation counter. The results, in terms of the amount of hybridized probe/chlorinekilled target as (CPM) on a scintillation counter, are presented in TABLE I.

TABLE I

| Hybridization Measurements of *E. coli* After Being Exposed to 32 ppm of Free Available Chlorine (FAC) | |
|---|---|
| Test Sample | Radioactivity Retained Counts Per Minute* (CPM) |
| Negative Control (no *E. coli* used) | 206 |
| Positive Control (*E. coli* but no chlorine treatment) | 933 |
| Test 1 - 5-min Chlorine Treatment | 288 |
| Test 2 - 30-min Chlorine Treatment | 169 |

*Background of 22 CPM subtracted.

Neither the 5-minute nor the 30-minute chlorine-treated sample containing chlorine-killed *E. coli* tested positive for the presence of living *E. coli* as shown by the much lower radioactivity value for Tests 1 and 2, as compared to the radioactivity value for live cells (positive control) Note that the values for CPM for Tests 1 and 2 are comparable to the negative control.

To confirm these results and determine the effect of lower chlorine concentrations, a second experiment was done with *E. coli*. Cells were exposed to 2 ppm FAC in distilled water for 5 minutes or for 2 hours. Only a sample of cells from the positive control was able to grow in culture. Therefore, cells were killed by a five-minute exposure to 2 ppm chlorine. The results are presented in TABLE II which follows.

TABLE II

| *E. coli* Exposed to 2 ppm FAC | |
|---|---|
| Test Sample | Radioactivity Retained Counts Per Minute* |
| Negative Control (no *E. coli* used) | 260 |
| Positive Control (*E. coli* but no chlorine treatment) | 1127 |
| Test 3 - 5-min Chlorine Treatment | 689 |
| Test 4 - 2-hr Chlorine Treatment | 348 |

*Background of 22 CPM subtracted.

The results given in TABLE II indicate that the 5 minute exposure time (Test 3) reduced the signal somewhat, while the longer exposure (Test 4) resulted in a signal close to that of the negative control.

Note that the levels of chlorine and exposure time used in this example were sufficient to kill *E. coli*. *E. coli* is 100 percent killed by a one-minute exposure to 0.055 ppm chlorine at room temperature and neutral pH (see the text Disinfection, Sterilization, and Preservation, edited by C. A. Lawrence and S. S. Block, Lea and Febiger, Philadelphia, 1968; p. 288).

The above two sets of experiments provide evidence that chlorine-killed cells are not detected with a probe for ribosomal RNA.

EXAMPLE 2

Comparison of Radioactive Labelled DNA Probe Detection of Killed *Legionella pneumophila* Versus Antibody Detection Method

(A) Probe Versus Antibody Detection

In the following two experiments, probe detection of chlorine-killed cells was compared with antibody detection. Probe assays were performed with Gen-Probe's "Rapid Diagnostic System for Legionella" kit. The kit contains: solubilizer (for clinical specimens), lysing reagent with glass beads, $^{125}$I-cDNA probe ($<1.0$ $\mu$Ci/40 ml), hydroxylapatite separation suspension, and buffered wash solution. The probe is a cDNA probe which detects only Legionella rRNA. Scintillation counting was done with CytoScint (a product of West Chem) in a Beckman LS-100C scintillation counter. The fluorescent-labelled antibody was purchased from BioDx. It identifies *L. pneumophila* serogroups 1-6 in direct fluorescent antibody (DFA) tests.

Approximately $5 \times 10^6$ *L. pneumophila* cells were added per ml of chlorine demand-free distilled water (e.g., water pretreated with chlorine to remove substances having chlorine demand so FAC levels can be maintained during experiments) containing 6.5 ppm FAC and held in an ice bath. Samples were removed and dechlorinated after 10, 30, 60, 90, and 160 minutes. For the positive control, cells were added to demand-free distilled water and chilled for 160 minutes. To determine viability of the cells, samples were streaked onto Legionella agar. Gen-Probe's test protocol for culture suspension was followed. Briefly, this protocol was as follows:

The sample was added to a lysing reagent tube and sonicated for 15 minutes at 60°-70° C. Probe solution was then added and hybridization was effected at 72° C. for one hour. The hydroxylapatite separation suspension was added and tubes were incubated for five minutes at 72° C. After centrifugation, wash solution was added. Following a five-minute incubation and centrifugation, the supernatant was decanted and CPM measured. Scintillation counting was done as described above in EXAMPLE 1.

To perform the DFA test, a sample portion was filtered through a 47 mm, 0.4 $\mu$m Nuclepore polycarbonate filter. A section of the filter was stained with the antibody and incubated at room temperature for 30 minutes. Excess antibody was removed by passing phosphate buffered saline (pH 7.4, 0.85 percent NaCl) through the membrane filter. The stained filter was then placed on a microscope slide with a glycerol carbonate buffer (pH 9.6). Stained cells (*L. pneumophila*) were observed with a fluorescence microscope.

The results are presented in TABLE III which follows.

TABLE III

| | *L. pneumophila* Exposed to 6.5 ppm of Available Chlorine | | | |
|---|---|---|---|---|
| | Probe Test Radioactivity Retained Counts per Minute | | Antibody DFA Test* | |
| Sample | Ex. 1 | Ex. 2 | Ex. 1 | Ex. 2 |
| Negative Control (no bacteria) | 488 | 284 | neg | neg |
| Positive Control (bacteria not chlorine-treated) | 7763 | 6670 | pos | pos |
| 10-Minute Chlorine exposure | 7112 | 4957 | pos | pos |
| 30-Minute Chlorine exposure | 811 | 458 | — | — |
| 60-Minute Chlorine exposure | 367 | 322 | — | — |
| 90-Minute Chlorine exposure | 364 | 320 | — | — |
| 160-Minute Chlorine exposure | 213 | 243 | pos | pos |

*Positive result means that cells exhibit yellowish-green fluorescence. The degree of brightness was the same for untreated and treated cells.

As the data given in TABLE III above shows, cells treated with 6.5 ppm available chlorine were negative with respect to hybridization in the probe assay after 30–60 minutes of chlorine exposure. Since the 10 minute chlorine treatment was sufficient to kill the bacteria, as evidenced by culture tests, an exposure to chlorine of at least thirty minutes is preferred before conducting the probe test to insure that chorine-killed cells are not detected. In contrast to these results using the probe, the samples were positive after 160 minutes of chlorine exposure using the antibody method. Therefore, the antibody method is unsuitable for use in chlorine-treated water for detection of only live bacteria.

(B) Testing of MAB in ELISA

This experiment was designed to test whether or not chlorine-killed *L. pneumophila* is also detected by a monoclonal antibody (MAB) in an enzyme linked immunosorbent assay (ELISA). In this experiment, detection of chlorine-killed cells was compared with formalin-killed cells instead of live cells. Killing of cells with formalin is a standard procedure often used when performing antibody tests, and the formalin does not interfere with detection.

*L. pneumophia* cells were exposed to 1.5-2.0 ppm FAC and held at room temperature for two days or killed with one percent formalin. Killed cells were diluted in carbonate buffer, pH 9.6, and adsorbed in microtiter plate wells. Legionella cells were detected with an unlabelled monoclonal antibody (obtained from Dr. W. Johnson, University of Iowa) and a goat anti-mouse antibody linked to peroxidase. ELISA assays were run in a standard manner. The results are presented in TABLE IV below.

TABLE IV

| | *L. pneumophila* Microtiter Plate ELISA Chlorine Killed vs. Formalin Killed Cells | | | |
|---|---|---|---|---|
| Peroxidase Reaction Time | Chlorinated | | Formalinized | |
| | Cells/Well | Mean Minus Blank $OD_{405}$ | Cells/Well | Mean Minus Blank $OD_{405}$ |
| 10 min | $5 \times 10^6$ | 0.390 | $1.2 \times 10^6$ | 0.164 |
| 20 min | $5 \times 10^6$ | 0.588 | $1.2 \times 10^6$ | 0.257 |
| 30 min | $5 \times 10^6$ | 0.782 | $1.2 \times 10^6$ | 0.346 |

This data demonstrate that antiboides can detect chlorine-killed *L. pneumophila*, using an ELISA assay.

Therefore, this method is unsuitable for use with chlorine-treated water since "false positive" results based on the presence of dead cells would occur.

EXAMPLE 3

Use of Enzyme Labelled Probe in Ultrafiltration Assays to Demonstrate *Campylobacter jejuni* Chromosomal DNA From Chlorine-Killed Cells is not Detected In addition to destruction of target rRNA, chlorine treatment also resulted in degradation of chromosomal DNA. This was demonstrated in two experiments using E. I. du Pont de Nemour & Co.'s SNAP *C. jejuni* probe. The probe is a single-stranded synthetic oligonucleotide 20 to 26 bases long conjugated with the enzyme alkaline phosphatase. It is a probe against a chromosomal DNA sequence. Separation of hybridized from unhybridized probe was accomplished by hybridization in solution followed by ultrafiltration separation as described below.

Ultrafiltration separation allowed hybridization to take place in solution. A lysate of *C. jejuni* cells (target DNA) was boiled in test tubes for 4 minutes in 0.48M phosphate buffer (pH 6.8). The tubes were transferred to a 50° C. water bath and the probe added to them immediately. Hybridization time was 30 minutes. Hybridized probe was separated as described in the patent application cited using a polyslyufone 50K MWCO ultrafiltration membrane (Schleicher & Schuell) and two washes of 5×SSC and one of phosphatase buffer (22 mM $Na_2CO_3$, 28 mM $NaHCO_2$, 1 mm $MgCl_2$). Probe was visulaized using a phosphatase buffer solution of the substrate disodium p-nitrophenyl phosphate which is enzymatically catalyzed to a yellow product by alkaline phosphatase.

The optical density was measured spectrophotometrically in a 1 cm pathlength tube at 405 n. Color appearance indicates enzyme, therefore, probe filter retention. The positive control employed cells not exposed to chlorine. The negative control had no cells and therefore no target DNA; no hybridization and no retention of probe by the filter should have occurred. Enzyme catalyzed colorimetric reaction time is indicated.

In the first experiment, *C. jejuni* cells ($10^7$/ml) were exposed to 5.6 ppm free available chlorine. In the second, $7 \times 10^7$/ml of these cells were treated with 6 ppm FAC.

TABLE V

Detection of Chlorine-Killed *C. jejuni* Nucleic Acid Using Ultrafiltration With an Enzyme-Labelled Probe

| Chlorine Exposure Time | Enzyme Reaction Time | | | |
|---|---|---|---|---|
| | 30 Min | 1 Hour | 2.7 Hours | 16 Hours |
| 1st Experiment (5.6 ppm FAC) | | | | |
| Positive Control | 0.12 | 0.17 | — | 1.00 |
| 15 minutes | 0.06 | 0.07 | — | 0.21 |
| 60 minutes | 0.04 | 0.04 | — | 0.03 |
| Negative Control | 0.04 | 0.04 | — | 0.16 |
| 2nd Experiment (6 ppm FAC) | | | | |
| Positive Control | 0.31 | 0.19 | 0.35 | |
| 5 minutes | 0.16 | 0.25 | 0.51 | |
| 20 minutes | 0.15 | 0.22 | 0.42 | |
| 60 minutes | 0.06 | 0.07 | 0.07 | |
| Negative Control | 0.05 | 0.05 | 0.05 | |

The above data shows that target chromosomal DNA was not detected after *C. jejuni* cells were chlorine-killed by being exposed to 5.6 or 6.0 ppm FAC for 60 minutes.

EXAMPLE 4

Chlorine Treatment of Autoclave-Killed Cells

In this example, *L. pneumophila* cells were autoclaved, and then optionally chlorine-treated following the procedure of EXAMPLE 2 above. In the first experiment, cells were merely autoclaved at 121° C. for 30 minutes or 90 minutes (no chlorine treatment). In the second experiment, this autoclaving was followed by chlorine-treatment.

The results are given in TABLE VI below.

TABLE VI

Autoclaving Versus Autoclaving Plus Chlorine Treatment

Experiment 1 - *L. pneumophila* Killed by Autoclaving (No chlorine)

| Sample | CPM* |
|---|---|
| Negative Control (no bacteria) | 171 |
| Positive Control (bacteria not autoclaved) | 2837 |
| Autoclaved 30 minutes | 2906 |
| Autoclaved 90 minutes | 1086 |

*Background of 24 CPM subtracted.

Experiment 2 - *L. pneumophila* Autoclaving Followed by Chlorine Exposure

| Sample | CPM* |
|---|---|
| Negative Control | 154 |
| Positive Control | 3510 |
| Autoclaved 30 minutes (unchlorinated control) | 802 |
| Autoclaved 30 minutes: | |
| 10 minutes chlorine exposure | 141 |
| 60 minutes chlorine exposure | 188 |
| 135 minutes chlorine exposure | 155 |

*Background of 25 CPM subtracted.

The results of the first experiment indicate that there was no signal reduction after 30 minutes and only a slight reduction in signal after 90 minutes of autoclaving. In the second experiment, cells autoclaved for 30 minutes at 121° C. tested positive in the probe assay but showed considerable signal loss. When these cells were exposed to 6 ppm available chlorine, the target was destroyed witin 10 minutes. These results indicate that exposure of either live or dead cells to chlorine treatment results in the destruction of target rRNA. This provides evidence that dead cells subsequently exposed to chlorine treatment will not be detected by nucleic acid probes. Therefore, false positive results will not be obtained.

Comparative Example A

Detection of Chloramine-Killed *Legionella penumophila* With a Radioactive Probe Because chlroamines are sometimes used in potable water treatment, their effect on nucleic acid targets was also tested. In the first experiment, a chloramine solution containing 6.0-6.4 ppm total chlorine was prepared in 10 mM phosphate buffer (pH 7) as described by N. R. Ward et al in 1984. The chlorine to nitrogen ratio was 2:1. Legionella cells ($5 \times 10^6$/ml) were added and samples taken at 60, 90 and 120 min. Although the test organism was not culturable at the first sampling time, the radioactive signal in the Gen-probe assay (described above) was not reduced after 120 minutes of exposure.

In the second experiment, the same $Cl_2$:N ratio was used but the exposure time was extended to five hours. Total chlorine was 6.75 ppm with only a trace of free chlorine present. As shown below, there was no reduction in signal. In the final experiment, the $Cl_2:N$ ratio was increased to 4:1. The combined chlorine concentration was 6 ppm. *L. pneumophila* cells ($5 \times 10^6$/ml) exposed to this solution for 23 hours at 4° C. were detected with the probe without signal reduction.

Data for the three experiments follows. Scintillation counting was done with CytoScint (a product of West Chem) in a Beckman LS-100C scintillation counter.

TABLE VII

Experiment 1
*L. pneumophila* Exposed to Chloramine
($Cl_2:N$ ratio = 2:1, total chlorine = 6.0–6.4 ppm)

| Sample | Treatment Time | CPM* |
|---|---|---|
| Negative Control (no bacteria) | — | 202 |
| Positive Control (bacteria not exposed to chloramine) | — | 3322 |
| No. 1 | 60 minutes | 3308 |
| No. 2 | 90 minutes | 3340 |
| No. 3 | 120 minutes | 3280 |

*Background of 22 CPM subtracted.

Experiment 2
*L. pneumophila* Exposed to Chloramine
($Cl_2:N$ ratio = 2:1, total chlorine = 6.75 ppm)

| Sample | Treatment Time | CPM* |
|---|---|---|
| Negative Control (no bacteria) | — | 349 |
| Positive Control (bacteria not exposed to chloramine) | — | 3547 |
| No. 1 | 2 hours | 3659 |
| No. 2 | 4 hours | 3377 |
| No. 3 | 5 hours | 3856 |

*Background of 20 CPM subtracted.

Experiment 3
*L. pneumophila* Exposed to Chloramine
($Cl_2:N$ ratio = 4:1, total chlorine = 6 ppm)

| Sample | Treatment Time | CPM* |
|---|---|---|
| Negative Control (no bacteria) | — | 154 |
| Positive Control (bacteria not exposed to chloramine) | — | 3510 |
| No. 1 | 2.5 hours | 3957 |
| No. 2 | 23 hours | 3684 |

*Background of 25 CPM subtracted.

In contrast to results with free available chlorine treatment described in the earlier examples, the data present in TABLE VII shows that rRNA in *L. pneumophila* was not destroyed even after 23 hours of exposure to chloramine.

EXAMPLE 5 and Comparative Example B

Testing of Additional Halogens: Bromine (EXAMPLE 5) and Iodine (Comparative Example B)

Experiments were done to determine if destruction of target nucleic acid sequences would result from bacterial exposure to other halogens. *L. pneumophila* cells exposed to 6.75 ppm free bromine in demand-free water showed slightly slower signal loss than in experiments with chlorine (60-90 minutes of bromine treatment being required versus 30-60 minutes of chlorine treatment to achieve essentially fyull loss of radioactive signal). It is noted that the test organism did not grow in culture after 10 minutes exposure, indicating that bromine-killing of the cells takes place in that short a time.

TABLE VIII

*L. pneumophila* Exposed to 6.75 ppm Free Bromine

| Sample | Treatment Time | CPM* |
|---|---|---|
| Negative Control (no bacteria) | — | 217 |
| Positive Control (bacteria not exposed to bromine) | — | 2208 |
| No. 1 | 10 minutes | 2458 |
| No. 2 | 60 minutes | 602 |
| No. 3 | 90 minutes | 360 |
| No. 4 | 120 minutes | 318 |
| No. 5 | 160 minutes | 241 |

*Background of 22 CPM subtracted.

Probe Hybridization With Killed-Cell Target Nucleic Acid of *L. pneumophila* in Iodine-Treated Water In contrast to the efficacy of the probe technique in not hybridizing with chlorine- or bromine-killed nucleic acid, iodine had no effect on the signal from *L. pneumophila* or *E. coli*. (Culturing showed that the test organisms did not grow after a 10 minute exposure to free iodine.) Gen-Probe's Legionella probe was used to detecdt *L. pneumophila* while their Mycoplasma II probe was used in the *E. coli* experiment.

Scintillation counting was done with CytoScint (a product of West Chem) in a Beckman LS-100C scintillation counter. The results are as follows:

TABLE IX (A)
*L. pneumophila* Exposed to 6.5 ppm Free Iodine

| Sample | Treatment Time | CPM* |
|---|---|---|
| Negative Control (no bacteria) | — | 480 |
| Positive Control (bacteria not exposed to iodine) | — | 5076 |
| No. 1 | 10 minutes | 5110 |
| No. 2 | 60 minutes | 5720 |
| No. 3 | 90 minutes | 5478 |
| No. 4 | 180 minutes | 5131 |

*Background of 24 CPM subtracted (B)
*E. coli* Exposed to 6.8 pm Free Iodine

| Sample | Treatment Time | CPM* |
|---|---|---|
| Negative Control | — | 456 |
| Positive Control | — | 931 |
| No. 1 | 10 minutes | 561 |
| No. 2 | 60 minutes | 619 |
| No. 3 | 90 minutes | 650 |
| No. 4 | 180 minutes | 637 |

*Background of 24 CPM subtracted.

"False positve " test results were obtained after three hours, as shown by the high CPM obtained from sample 4 (A) and 4 (B) in relationship to the positive control. These results indicate that the probe technique is unsuitable for use with iodine-treated water. Similar results were obtained using formalin-treated and hydrogen peroxide-treated water.

What is claimed is:

1. A method for selectively detecting the presence of live microorganisms in a mixture of live and dead microorganisms in chlorine- or bromine-treated water, and avoiding false-positive detection of said dead microorganisms, which comprises:

(a) lysing live microorganisms present in a sample of chlorine- or bromine-treated water and rendering constituent nucleic acid molecules single-stranded to provide single-stranded target nucleic acid molecules;

(b) contacting said single-stranded target nucleic acid molecules with single-stranded labelled probe nucleic acid molecules containing a sequence complementary to nucleic acid molecules of an indicator microorganism selected from the group consisting of *Escherichia coli, Legionella pneumophila*, and *Campylobater jejuni* to form labelled hybridized probe/target nucleic acid molecules;

(c) separating said labelled hybridized probe/target nucleic acid molecules from said single-stranded nucleic acid molecules using separation means; and (d) selectively detecting, by means of said label, nucleic acid molecules of said live microorganisms in said treated water.

2. The method of claim 1 wherein said separation emans is selected from the group consisting of ultrafiltration, membrane immobilization, the use of hydroxylapatite, and combinations thereof.

3. The method of claim 1 wherein said separation means is ultrafiltration.

4. The method of claim 3 wherein said ultrafiltration is effected usign a membrane filter having a pore size sufficient to pass single-stranded probe molecules but retain probe molecules hybridized by target nucleic acid.

5. The method of claim 4 wherein the membrane has a molecular weight cutoff of between about 50,000 and about 1,000,000 daltons.

6. The method of claim 1 wherein filtration is used prior to step (a) to concentrate waterborne microorganisms by passing said chlorine- or bromine-treated water through a membrane filter having a pore size sufficient to retain said microorganisms on said filter.

7. The method of claim 6 wherein said chlorine- or bromine-treated water is passed in a direction essentially perpendicular to a surface of the filter in order to effect filtration of said chlorine-or bromine-treated water.

8. The method of claim 6 wherein said chlorine- or bromine-treated water is passed in a direction essentially parallel to a surface of the filter in order to effect filtration of said chlorine- or bromine-treated water.

9. The method of claim 1 wherein said labelled hybridized probe/target nucleic acid molecules are quantified by means selected from the group consisting of chromogenic, fluorogenic, luminescent, and radioactive means.

10. A kit for selectively detecting the presence of live microorganisms in a mixture of live and dead microorganisms in chlorine- or bromine-treated water comprising:

(a) a sample of single-stranded labelled probe nucleic acid molecules containing a sequence complementary to nucleic acid molecules of an indicator microorganism selected from the group consisting of *Escherichia coli, Legionella pneumophila*, and *Campylobacter jejuni*, (b) a sample of live microorganisms in, or obtained from, chlorine- or bromine-treated water, (c) a lysing medium for providing single-stranded target nucleic acid molecules from within said live microorganisms, and (d) a medium for effecting separation of hybridized probe/target nucleic acid probe nucleic acid molecules.

11. The kit of claim 10 wherein said medium for effecting separation recited in step (d) is selected from the group consisting of a membrane filter, hydroxylapatite, an ultrafiltration membrane, and combinations thereof.

12. The kit of claim 10 which additionally contains a wash solution for washing unhybridized labelled probe nucleic acid molecules off or through said medium for effecting separation recited in step (d).

13. The kit of claim 10 wherein said labelled probe nucleic acid molecules contain an enzyme label and wherein said kit additionally contains an enzyme substrate to assist in identification of hybridized probe/target nucleic acid molecules.

14. The kit of claim 13 which additionally contains a buffer solution for said enzyme substrate to assist in identification of hybridized probe/target nucleic acid molecules.

* * * * *

UNITED STATES PATENT AND TRADEMARK OFFICE
CERTIFICATE OF CORRECTION

PATENT NO. : 5,004,682
DATED : April 2, 1991
INVENTOR(S) : Katherine P. Roberts et al.

It is certified that error appears in the above—identified patent and that said Letters Patent is hereby corrected as shown below:

- In Column 4, at line 1, delete "$3_H$" and insert --$3^H$--;
- In Colunm 8, at line 3, after "was" insert --found to have broad specification.--; at line 4, after "32" and before "phosphate" insert --ppm free available chlorine (FAC) in a 0.125 M--; and at line 44, after ")" and before "Note" insert --.--;
- In Column 10, at line 66 after "demonstrate" please insert --s--, so it reads "demonstrates" and delete "antiboides" and insert --antibodies--;
- In Column 11, at line 28 delete "polyslyufone" and insert -- polysulfone--; at line 31 delete "NaHCO$_3$, 1mm" and insert --NaHCO$_3$, 1$_m$mM--; and at line 37 after "405 n" please insert --$^m$--, so it reads "405 n$^m$".
- In Column 12, at line 54 delete "chlroamines" and insert --chloramines--;
- In Column 13, at line 64 , delete "fyull" and insert --full--;
- In Column 14, at line 25, delete "tecdt" and insert --tect--; and at line 43 after "6.8 p" insert --p-- so it will read --6.8 ppm--,
- In Column 15 at line 9 delete "Campylobater" and insert --Campylobacter--; at line 18 delete "emans" and insert --means--; and at line 24 delete "usign" and insert --using--; and
- In Column 16 at line 24 after "a..:d" and before "probe" insert --molecules from single-stranded labelled--.

Signed and Sealed this

Twenty-second Day of September, 1992

Attest:

DOUGLAS B. COMER

Attesting Officer          Acting Commissioner of Patents and Trademarks